United States Patent
Marom et al.

(10) Patent No.: US 9,206,197 B2
(45) Date of Patent: Dec. 8, 2015

(54) AMORPHOUS FORM OF DOLUTEGRAVIR

(75) Inventors: Ehud Marom, Kfar Saba (IL); Shai Rubnov, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 14/344,737

(22) PCT Filed: Sep. 2, 2012

(86) PCT No.: PCT/IL2012/050344
§ 371 (c)(1),
(2), (4) Date: Mar. 13, 2014

(87) PCT Pub. No.: WO2013/038407
PCT Pub. Date: Mar. 21, 2013

(65) Prior Publication Data
US 2014/0350004 A1    Nov. 27, 2014

Related U.S. Application Data

(60) Provisional application No. 61/534,395, filed on Sep. 14, 2011.

(51) Int. Cl.
*C07D 498/14* (2006.01)

(52) U.S. Cl.
CPC .................................. *C07D 498/14* (2013.01)

(58) Field of Classification Search
CPC ..................................................... C07D 498/14
USPC ........................................ 544/95; 514/230.2
See application file for complete search history.

(56) References Cited

U.S. PATENT DOCUMENTS

2009/0318421 A1    12/2009   Johns

FOREIGN PATENT DOCUMENTS

| WO | 2006116764 A1 | | 11/2006 |
|---|---|---|---|
| WO | WO 2006116764 A1 | * | 11/2006 |
| WO | 2010011812 A1 | | 1/2010 |
| WO | 2010011819 A1 | | 1/2010 |
| WO | WO 2010011812 A1 | * | 1/2010 |
| WO | WO 2010011819 A1 | * | 1/2010 |
| WO | 2010068253 A1 | | 6/2010 |

OTHER PUBLICATIONS

L. Yu, "Amorphous Pharmaceutical Solids: Preparation, Characterization and Stabilization"; Advanced Drug Delivery Reviews, vol. 48, Issue 1, p. 27-42, (May 16, 2001).*
Brittain H. G. "Polymorphism in Pharmaceutical Solids", Edited by, p. 7-8, 184-220; Marcel Dekker, Inc. (1999).*
Brittain (1999), Polymorphism in Pharmaceutical Solids, edited by Brittain, pp. 184-226; Marcel Dekker, Inc. New York, NY, 45 pages.
Brittain (1999), Polymorphism in Pharmaceutical Solids, edited by Brittain, pp. 7-8; Marcel Dekker, Inc. New York, NY, 6 pages.
Byrn et al., (1995) Pharmaceutical solids: a strategic approach to regulatory considerations. Pharm Res 12(7): 945-54, 10 pages.
Hancock and Parks (2000) What is the true solubility advantage for amorphous pharmaceuticals? Pharm Res 17(4): 397-404, 8 pages.
Hancock et al., (2002) Polyamorphism: a pharmaceutical science perspective. J Pharm Pharmacol 54(8): 1151-2, 2 pages.
Yu (2001) Amorphous pharmaceutical solids: preparation, characterization and stabilization. Adv Drug Deliv Rev 48(1): 27-42, 16 pages.

* cited by examiner

*Primary Examiner* — Kahsay Habte
(74) *Attorney, Agent, or Firm* — Rothwell, Figg, Ernst & Manbeck, P.C.

(57) ABSTRACT

An amorphous form of dolutegravir sodium, pharmaceutical compositions comprising same, methods for its preparation and use thereof as an antiretroviral agent.

14 Claims, 11 Drawing Sheets

AMORPHOUS FORM OF DOLUTEGRAVIR

CROSS REFERENCE TO RELATED APPLICATIONS

This application is a 35 U.S.C. §371 National Phase Entry Application from PCT/IL2012/050344, filed Sep. 2, 2012, and designating the United States, which claims priority to U.S. Patent Application No. 61/534,395 filed Sep. 14, 2011, which are incorporated herein in their entireties.

FIELD OF THE INVENTION

The present invention relates to an amorphous form of dolutegravir (GSK1349572), pharmaceutical compositions comprising same, and use thereof in treating retroviral infections, especially human immunodeficiency virus (HIV) infection.

BACKGROUND OF THE INVENTION

Dolutegravir (DTG, GSK1349572) is an integrase inhibitor being developed for the treatment of human immunodeficiency virus (HIV)-1 infection.

Dolutegravir sodium is chemically named sodium (4R,12aS)-9-((2,4-difluorobenzyl)carbamoyl)-4-methyl-6,8-dioxo-3,4,6,8,12,12a-hexahydro-2H-pyrido[1',2':4,5]pyrazino[2,1-b][1,3]oxazin-7-olate and is represented by the following chemical structure:

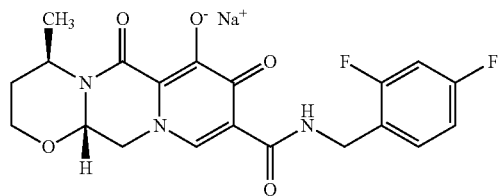

A new crystalline or amorphous form of a compound may possess physical properties that differ from, and are advantageous over, those of other crystalline or amorphous forms. These include, packing properties such as molar volume, density and hygroscopicity; thermodynamic properties such as melting temperature, vapor pressure and solubility; kinetic properties such as dissolution rate and stability under various storage conditions; surface properties such as surface area, wettability, interfacial tension and shape; mechanical properties such as hardness, tensile strength, compactibility, handling, flow and blend; and filtration properties. Variations in any one of these properties may affect the chemical and pharmaceutical processing of a compound as well as its bioavailability and may often render the new form advantageous for pharmaceutical and medical use.

Dolutegravir and processes for its preparation are disclosed in WO 2010/068253 and US 2009/0318421. WO 2010/068253 discloses a crystalline form of dolutegravir sodium salt characterized by the following diffraction peaks in the X-ray powder diffraction pattern at 6.4°±0.2°, 9.2°±0.2°, 13.8°±0.2°, 19.2°±0.2° and 21.8°±0.2° degrees two-theta; and the following characteristic peaks in the infrared absorption spectrum at 1641±2, 1536±2, 1503±2 and 1424±2 cm$^{-1}$; and a crystalline form of dolutegravir sodium hydrate characterized by the following diffraction peaks in the X-ray powder diffraction pattern at 8.0°±0.2°, 9.3°+0.2°, 11.3°±0.2°, 16.0°±0.2° and 22.8°±0.2° degrees two-theta; and the following characteristic peaks in the infrared absorption spectrum at 1637±2, 1536±2, 1501±2 and 1422±2 cm$^{-1}$. Further disclosed in WO 2010/068253 is a crystalline form of dolutegravir characterized by the following diffraction peaks in the X-ray powder diffraction pattern at 5.4°±0.2°, 10.7°±0.2°, 12.3°±0.2°, 15.2°±0.2° and 16.4°±0.2° degrees two-theta; and the following characteristic peaks in the infrared absorption spectrum at 1658±2, 1628±2, 1540±2 and 1498±2 cm$^{-1}$.

There still remains an unmet need for solid state forms of dolutegravir having good physicochemical properties, desirable bioavailability, and advantageous pharmaceutical parameters.

SUMMARY OF THE INVENTION

The present invention provides a new amorphous form of dolutegravir sodium, pharmaceutical compositions comprising same, methods for its preparation and use thereof as an anti-HIV agent.

The present invention is based in part on the unexpected finding that the new amorphous form disclosed herein possesses advantageous physicochemical properties which render its processing as a medicament beneficial. The new form of the present invention has advantageous solubility properties as compared to the crystalline forms of WO 2010/068253. Consequently, the amorphous form of the present invention may possess good bioavailability which would enable its easy formulation into a variety of solid dosage forms.

According to one aspect, the present invention provides an amorphous form of dolutegravir sodium. In one embodiment, the amorphous form of dolutegravir sodium is characterized by an X-ray diffraction (XRD) profile substantially as shown in any of FIGS. 1, 6A or 7. Each possibility represents a separate embodiment of the present invention. In another embodiment, the present invention provides an amorphous form of dolutegravir sodium characterized by a DSC profile substantially as shown in FIG. 2 or 8. Each possibility represents a separate embodiment of the present invention. In yet another embodiment, the amorphous form of dolutegravir sodium has a glass transition temperature between about 130° C. and about 210° C., for example about 133° C., or about 208° C. Each possibility represents a separate embodiment of the present invention. In some embodiments, the glass transition onset temperature of the amorphous dolutegravir sodium of the present invention is from about 95° C. to about 202° C. In another embodiment, the amorphous form of dolutegravir sodium is characterized by a TGA profile substantially as shown in FIG. 3 or 9. Each possibility represents a separate embodiment of the present invention. In other embodiments, the amorphous form is characterized by an IR spectrum substantially as shown in FIG. 4 or 10. Each possibility represents a separate embodiment of the present invention. In some embodiments, the IR spectrum of the amorphous form of dolutegravir sodium comprises characteristic peaks at about 662±4, 766±4, 851±4, 886±4, 959±4, 1025±4, 1055±4, 1090±4, 1133±4, 1206±4, 1233±4, 1248±4, 1279±4, 1318±4, 1356±4, 2325±4 and 2348±4 cm$^{-1}$. In other embodiments, the IR spectrum of the amorphous form of dolutegravir sodium further comprises characteristic peaks at about 650±4, 685±4, 805±4, 1422±4, 1472±4, 1499±4, 1538±4 and 1627±4 cm$^{-1}$. In certain embodiments, the amorphous form of dolutegravir sodium is characterized by a Raman spectrum substantially as shown in FIG. 5 or 11. Each possibility represents a separate embodiment of the invention. In particular embodiments, the Raman spectrum of the amorphous dolutegravir sodium of the present invention comprises characteristic peaks at about 62±4, 239±4, 333±4, 423±4, 484±4, 531±4, 585±4, 619±4, 688±4, 738±4, 787±4, 862±4, 917±4, 968±4, 1012±4, 1104±4, 1154±4, 1203±4, 1246±4, 1277±4, 1323±4, 1400±4, 1428±4, 1470±4, 1515±4, 1588±4, 1650±4, 2875±4, 2940±4, 2983±4 and 3082±4 cm$^{-1}$.

In one embodiment, the present invention provides a process for preparing amorphous dolutegravir sodium, comprising the step of grinding or milling a dolutegravir sodium (e.g., crystalline dolutegravir sodium) so as to provide amorphous dolutegravir sodium. Preferably, the milling is conducted for a time period ranging between about 10 minutes and about 500 minutes, more preferably for a time period ranging between about 200 minutes to about 400 minutes.

In another embodiment, the present invention provides a process for preparing amorphous dolutegravir sodium, the process comprising the steps of:
(a) dissolving dolutegravir sodium in water; and
(b) freeze-drying or lyophilizing the solution obtained in step (a), so as to provide amorphous dolutegravir sodium.

In certain embodiments, the present invention provides a pharmaceutical composition comprising the amorphous dolutegravir sodium of the present invention as an active ingredient, and a pharmaceutically acceptable carrier.

In a particular embodiment, the pharmaceutical composition is in the form of a tablet. In one embodiment, the amorphous dolutegravir sodium of the present invention is useful for treating retroviral infections, especially human immunodeficiency virus (HIV) infection.

In various embodiments, the present invention provides a pharmaceutical composition comprising the amorphous dolutegravir sodium of the present invention as an active ingredient, and a pharmaceutically acceptable carrier for use in treating retroviral infections, especially human immunodeficiency virus (HIV) infection.

In some embodiments, the present invention provides a method of treating retroviral infections, especially human immunodeficiency virus (HIV) infection comprising administering to a subject in need thereof an effective amount of the amorphous dolutegravir sodium of the present invention, or a pharmaceutical composition comprising the amorphous dolutegravir sodium of the present invention.

In additional embodiments, the present invention provides the use of the amorphous dolutegravir sodium of the present invention for treating retroviral infections, especially human immunodeficiency virus (HIV) infection.

In other embodiments, the subject is a mammal, preferably a human.

Further embodiments and the full scope of applicability of the present invention will become apparent from the detailed description given hereinafter. However, it should be understood that the detailed description and examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention is directed to a novel amorphous form of sodium (4R,12aS)-9-((2,4-difluorobenzyl)carbamoyl)-4-methyl-6,8-dioxo-3,4,6,8,12,12a-hexahydro-2H-pyrido[1',2':4,5]pyrazino[2,1-b][1,3]oxazin-7-olate (dolutegravir sodium).

The present invention is further directed to pharmaceutical compositions comprising the amorphous form of the present invention and a pharmaceutically acceptable carrier and their use in treating retroviral infections.

The present invention is further directed to methods of preparing the novel amorphous form of the present invention.

Polymorphs are two or more solid state phases of the same chemical compound that possess different arrangement and/or conformation of the molecules. Polyamorphism is the ability of a substance to exist in several different amorphous forms. Different forms of amorphous pharmaceuticals with readily discernible physical and chemical characteristics and some marked differences in their pharmaceutical performance have been reported. Even though amorphous materials do not exhibit long-range periodic atomic ordering, different amorphous phases of the same chemical substance can exhibit significant structural differences in their short-range atomic arrangement. These differences may lead to different physical and chemical properties such as density, stability, processability, dissolution and even bioavailability. Polyamorphism in pharmaceuticals is reviewed in Hancock et al. (Journal of Pharmacy and Pharmacology 2002, 54: 1151-1152), the content of which is hereby incorporated by reference. The identification and characterization of various morphic or amorphic forms of a pharmaceutically active compound is of great significance in obtaining medicaments with desired properties including a specific dissolution rate, milling property, bulk density, thermal stability or shelf-life. The novel amorphous form of dolutegravir sodium disclosed herein possesses improved physicochemical properties including advantageous solubility properties.

Figure 1:
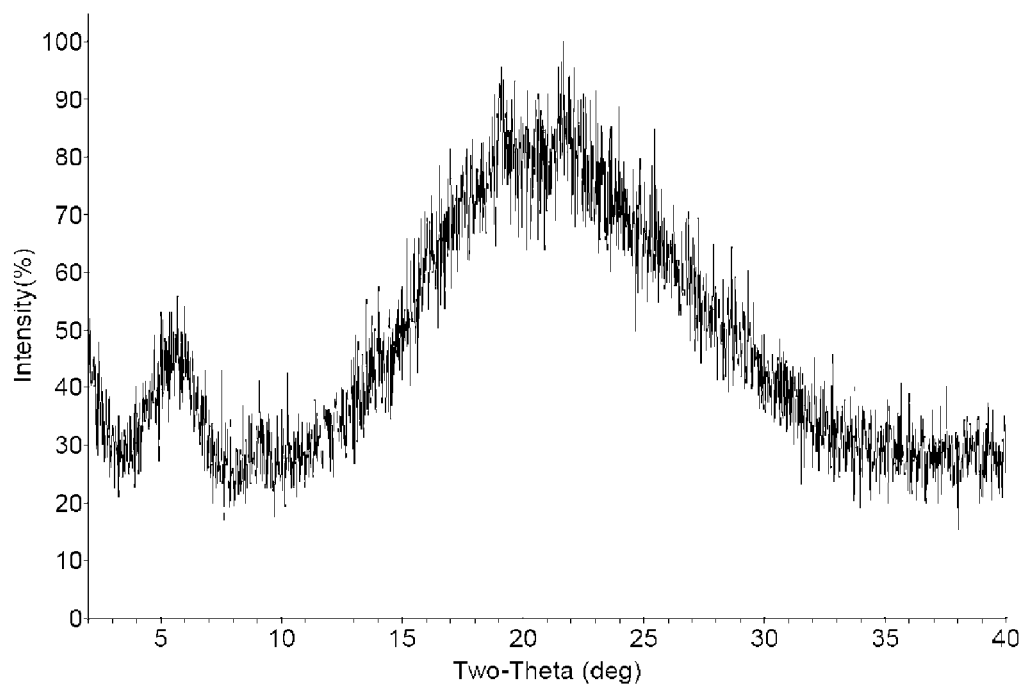
FIG. 1 illustrates a characteristic X-ray diffraction pattern of an amorphous form of dolutegravir sodium obtained by method I.
Figure 6:
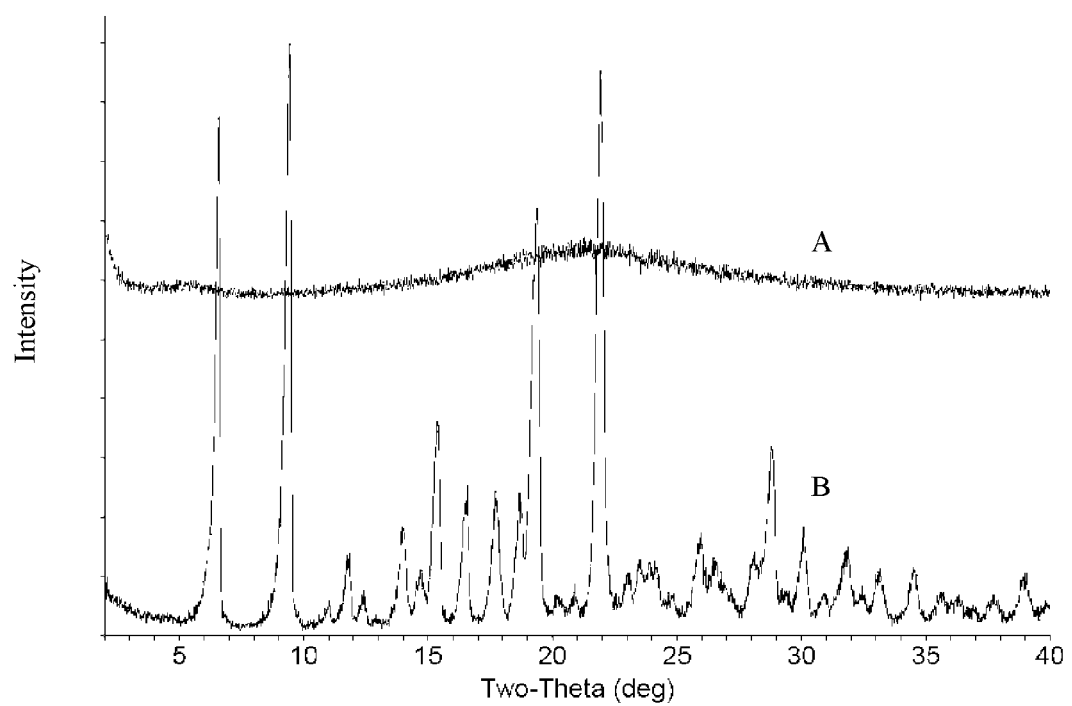
FIG. 6 illustrates a characteristic X-ray diffraction pattern of an amorphous form of dolutegravir sodium obtained by method II (panel A). Also shown for comparison is the X-ray diffraction pattern of crystalline dolutegravir sodium From I of WO 2010/068253 (panel B).
Figure 7:
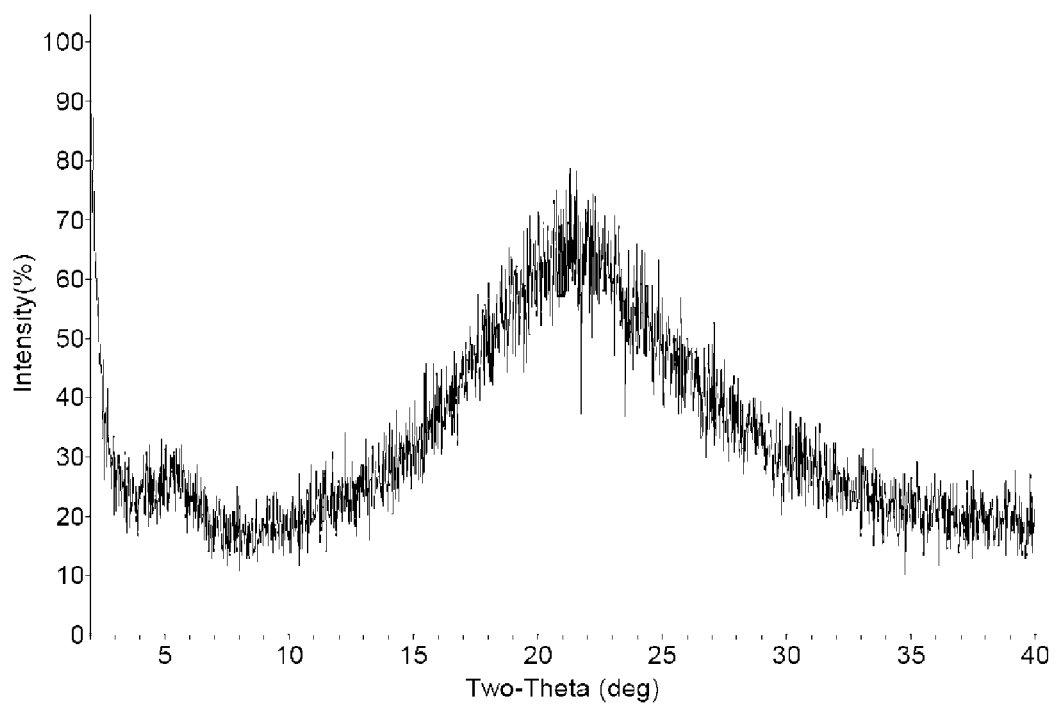
FIG. 7 illustrates a characteristic X-ray diffraction pattern of an amorphous form of dolutegravir sodium obtained by method H.

In one embodiment, the present invention provides an amorphous form of dolutegravir sodium which is characterized by an X-ray diffraction pattern having a single broad peak expressed between about 10 and about 30 degrees two theta [2θ°] as is shown in any of FIGS. 1, 6A or 7. Each possibility represents a separate embodiment of the present invention. In some embodiments, the amorphous form is further characterized by its glass transition temperature and by using various techniques including, but not limited to, infrared spectroscopy, Raman spectrometry, and thermal analysis (e.g. thermogravimetric analysis (TGA) and differential scanning calorimetry (DSC)).

Figure 2:
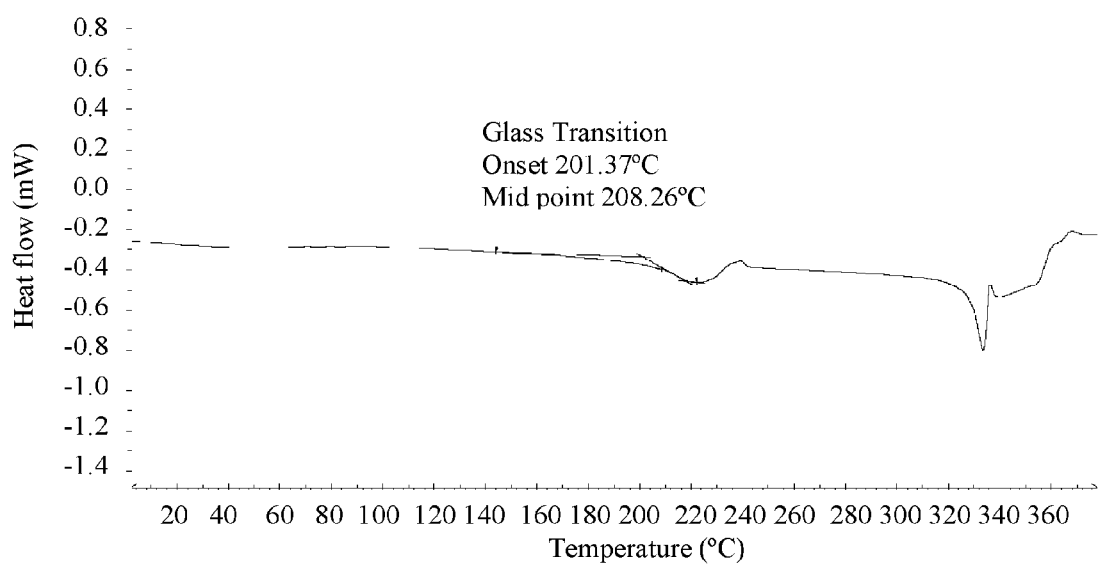
FIG. 2 illustrates a characteristic Differential Scanning Calorimetry (DSC) profile of an amorphous form of dolutegravir sodium obtained by method I.
Figure 8:
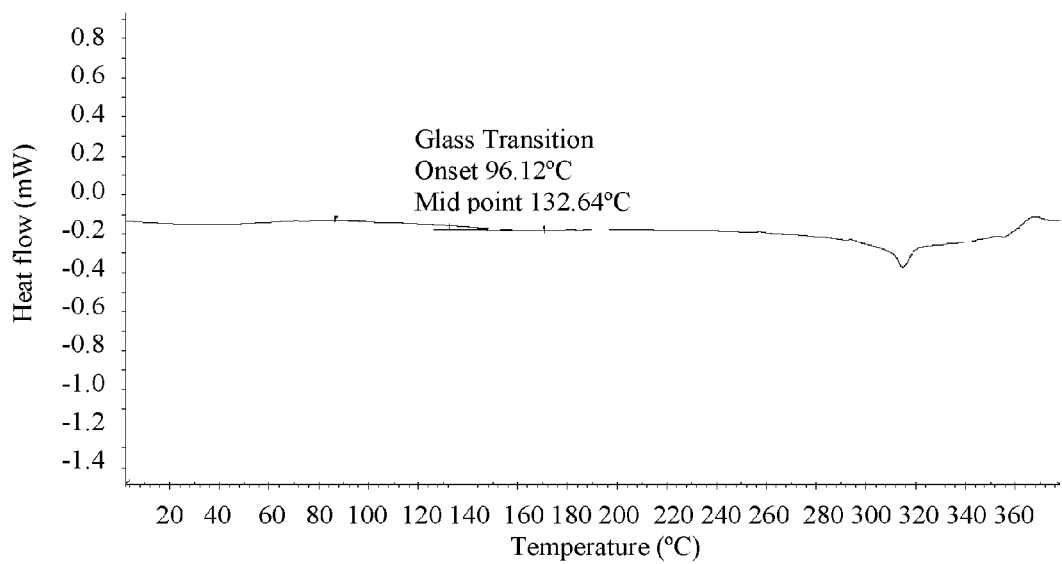
FIG. 8 illustrates a characteristic Differential Scanning Calorimetry (DSC) profile of an amorphous form of dolutegravir sodium obtained by method II.

In one embodiment, the amorphous form of dolutegravir sodium of the present invention is characterized by a DSC profile substantially as shown in either of FIG. 2 or 8. Each possibility represents a separate embodiment of the present invention. In another embodiment, the amorphous form of dolutegravir sodium of the present invention is further characterized by a TGA profile substantially as shown in either of FIG. 3 or 9. Each possibility represents a separate embodiment of the present invention. In other embodiments, the amorphous form has a glass transition temperature between about 130° C. and about 210° C. In some embodiments, the glass transition temperature of amorphous dolutegravir sodium is about 133° C. In other embodiments, the glass transition temperature of amorphous dolutegravir sodium is about 208° C. In yet other embodiments, the glass transition onset temperature of amorphous dolutegravir sodium is between about 95° C. and about 202° C. In another embodiment, the amorphous dolutegravir sodium of the present invention is characterized by an infrared spectrum substantially as shown in either of FIG. 4 or 10 with characteristic peaks at the following wavenumbers: about 662, about 766, about 851, about 886, about 959, about 1025, about 1055, about 1090, about 1133, about 1206, about 1233, about 1248, about 1279, about 1318, about 1356, about 2325, and about 2348 cm$^{-1}$. In further embodiments, the infrared spectrum further comprises characteristic peaks at the following wavenumbers: about 650, about 685, about 805, about 1422, about 1472, about 1499, about 1538, and about 1627±4 cm$^{-1}$. In other embodiments, the amorphous form of dolutegravir sodium of the present invention is characterized by a Raman spectrum substantially as shown in either of FIG. 5 or 11 with characteristic peaks at the following wavenumbers: about 62, about 239, about 333, about 423, about 484, about 531, about 585, about 619, about 688, about 738, about 787, about 862, about 917, about 968, about 1012, about 1104, about 1154, about 1203, about 1246, about 1277, about 1323, about 1400, about 1428, about 1470, about 1515, about 1588, about 1650, about 2875, about 2940, about 2983, and about 3082 cm$^{-1}$. Each possibility represents a separate embodiment of the present invention.

In other embodiments, the present invention further provides processes for the preparation of amorphous dolutegravir sodium. In one embodiment, these processes involve the use of dolutegravir, such as crystalline dolutegravir sodium as the starting material or any other dolutegravir sodium prepared by any methods known in the art. Alternatively, dolutegravir enol made in accordance with any method known in the art, including, for example, the methods described in WO 2010/068253 and US 2009/0318421, the contents of each of which are hereby incorporated by reference in their entirety, and converted to its sodium salt by conventional methods, can be used as the starting material in the processes of the present invention. According to one embodiment, the dolutegravir sodium starting material is subjected to high pressure (e.g. grinding or milling) using various forces and time intervals to afford the conversion of crystalline dolutegravir sodium to amorphous dolutegravir sodium. According to another embodiment, the dolutegravir sodium starting material is dissolved in water. The water is then removed using freeze drying (lyophilization).

The novel amorphous form of the present invention is useful for the treatment of retroviral infections including, in particular, human immunodeficiency virus (HIV) infection (e.g. HIV-1 infection). The present invention thus provides pharmaceutical compositions comprising amorphous dolutegravir sodium and a pharmaceutically acceptable carrier. The pharmaceuticals can be safely administered orally or non-orally. Routes of administration include, but are not limited to, oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual. Typically, the amorphous dolutegravir sodium of the present invention is administered orally. The pharmaceutical compositions can be formulated as tablets (including e.g. film-coated tablets and orally disintegrating tablets), powders, granules, capsules (including soft capsules), and sustained-release preparations as is well known in the art.

Pharmacologically acceptable carriers that may be used in the context of the present invention include various organic or inorganic carriers including, but not limited to, excipients, lubricants, binders, disintegrants, water-soluble polymers and basic inorganic salts. The pharmaceutical compositions of the present invention may further include additives such as, but not limited to, preservatives, antioxidants, coloring agents, sweetening agents, souring agents, bubbling agents and flavorings.

Suitable excipients include e.g. lactose, D-mannitol, starch, cornstarch, crystalline cellulose, light silicic anhydride and titanium oxide. Suitable lubricants include e.g. magnesium stearate, sucrose fatty acid esters, polyethylene glycol, talc and stearic acid. Suitable binders include e.g. hydroxypropyl cellulose, hydroxypropylmethyl cellulose, crystalline cellulose, a-starch, polyvinylpyrrolidone, gum arabic powder, gelatin, pullulan and low-substitutional hydroxypropyl cellulose. Suitable disintegrants include e.g. crosslinked povidone (any crosslinked 1-ethenyl-2-pyrrolidinone homopolymer including polyvinylpyrrolidone (PVP) and 1-vinyl-2-pyrrolidinone homopolymer), crosslinked carmellose sodium, carmellose calcium, carboxymethyl starch sodium, low-substituted hydroxypropyl cellulose, cornstarch and the like. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum and the like.

Suitable preservatives include e.g. sodium benzoate, benzoic acid, and sorbic acid. Suitable antioxidants include e.g. sulfites, ascorbic acid and α-tocopherol. Suitable coloring agents include e.g. food colors such as Food Color Yellow No. 5, Food Color Red No. 2 and Food Color Blue No. 2 and the like. Suitable sweetening agents include e.g. dipotassium glycyrrhetinate, aspartame, stevia and thaumatin. Suitable souring agents include e.g. citric acid (citric anhydride), tartaric acid and malic acid. Suitable bubbling agents include e.g. sodium bicarbonate. Suitable flavorings include synthetic substances or naturally occurring substances, including e.g. lemon, lime, orange, menthol and strawberry.

The amorphous dolutegravir sodium of the present invention is particularly suitable for oral administration in the form of tablets including sublingual tablets and orally disintegrating tablets, capsules, pills, dragées, powders, granules, orally disintegrating wafers, and the like. A tablet may be made by compression or molding, optionally with one or more excipients as is known in the art. For example, molded tablets may be made by molding in a suitable machine a mixture of the powdered active ingredient moistened with an inert liquid diluent.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in micro-encapsulated form, if appropriate, with one or more of the above-described excipients.

The present invention provides a method of treating retroviral infections including, but not limited to, HIV infection comprising administering to a subject in need thereof a therapeutically effective amount of a composition comprising amorphous dolutegravir sodium, for example the amorphous dolutegravir sodium described herein.

"A therapeutically effective amount" as used herein refers to an amount of an agent which is effective, upon single or multiple dose administration to the subject in providing a therapeutic benefit to the subject. In one embodiment, the therapeutic benefit is inducing an antiretroviral effect. In additional embodiments, the amorphous dolutegravir sodium of the present invention is used for the preparation of an antiretroviral medicament.

The present invention further provides the administration of the amorphous dolutegravir sodium of the present invention in combination therapy with one or more other active ingredients, for example other anti-retroviral drugs. The combination therapy may include the two or more active ingredients within a single pharmaceutical composition as well as the two or more active ingredients in two separate pharmaceutical compositions administered to the same subject simultaneously or at a time interval determined by a skilled artisan.

The principles of the present invention are demonstrated by means of the following non-limiting examples.

EXAMPLES

Example 1

General Preparation Methods of Amorphous Dolutegravir Sodium

1. Instruments
Sartorius CP 225D Balance
ELGA Water Purification Equipment
Mettler Toledo DSC 1
TA Q5000IR TGA
Rigaku D/MAX 2200 X-ray powder diffractometer
Thermo Nicolet 380 FT-IR
Eyela FDU-1100 freeze dryer
Jobin Yvon LabRam-1B FT-Raman 2. XRPD, DSC, TGA, FT-IR, and FT-Raman
2.1 XRPD method
Details of XRPD method used in the tests are mentioned below:
X-ray Generator: Cu, ka, (λ=1.54056 Å).
Tube Voltage: 40 kV, Tube Current: 40 mA.
DivSlit: 1 deg.
DivH.L.Slit: 10 mm
SctSlit: 1 deg.
RecSlit: 0.15 mm
Monochromator: Fixed Monochromator
Scanning Scope: 2-40 deg.
Scanning Step: 10 deg/min
2.2 DSC and TGA methods
Details of DSC method used in the tests are mentioned below:
Heating from 30° C. to 380° C. at 10° C./min
Details of TGA method used in the tests are mentioned below:
Heating from 30° C. to 450° C. at 10° C./min
2.3 FT-IR and FT-Raman methods
Details of FT-IR method used in the tests are mentioned below:
No. of scan: 32
Time for collection: 38 s
Scan Range: 600-4000 $cm^{-1}$
Resolution: 4 $cm^{-1}$
Details of FT-Raman method used in the tests are mentioned below:
Laser wave: 632.8 nm
Power: 1 mW
Resolution: 1 $cm^{-1}$
Time for integration: 50 s
3. General Preparation Methods
3.1 Method I: Grinding
Dolutegravir sodium (e.g., From I of WO 2010/068253) was milled by using planetary mono mill at 200 rpm for 200 or 400 min. Amorphous dolutegravir sodium was identified by this method, as set forth in the Examples below. Grinding for shorter periods of times (10-30 minutes) also showed a trend towards forming amorphous dolutegravir sodium.
3.2 Method II: Lyophilization
About 100 mg of Dolutegravir sodium (e.g., From I of WO 2010/068253) were dissolved in 300 ml of water. The water was then removed by freeze-drying (lyophilization). Amorphous dolutegravir sodium was identified by this method, as set forth in the Examples below.

Example 2

Amorphous Dolutegravir Sodium (Method I)

Figure 3:
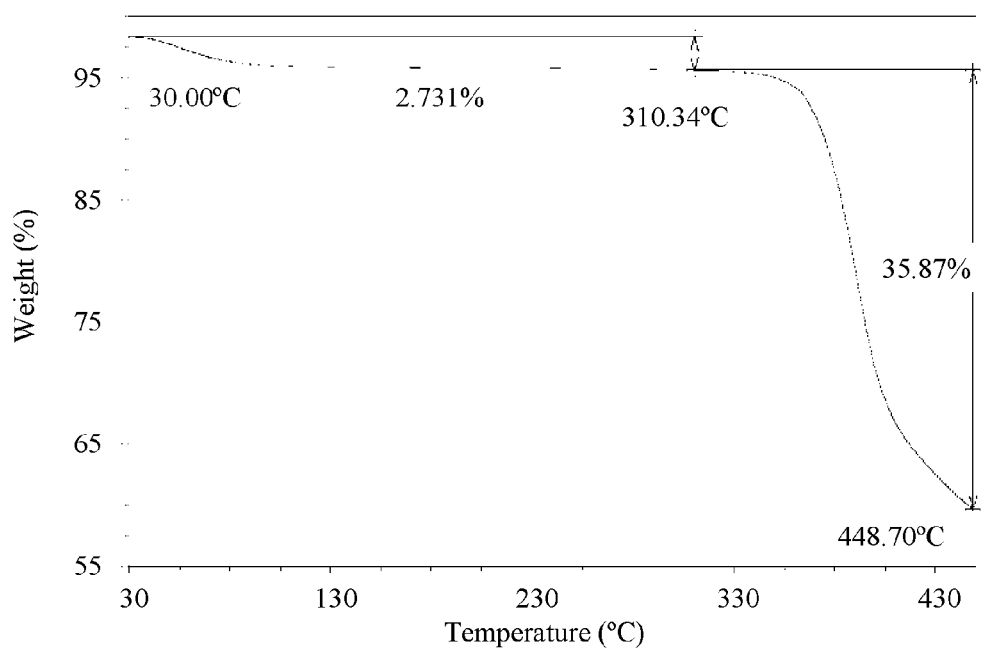
FIG. 3 illustrates a characteristic Thermogravimetric analysis (TGA) profile of an amorphous form of dolutegravir sodium obtained by method I.
Figure 4:
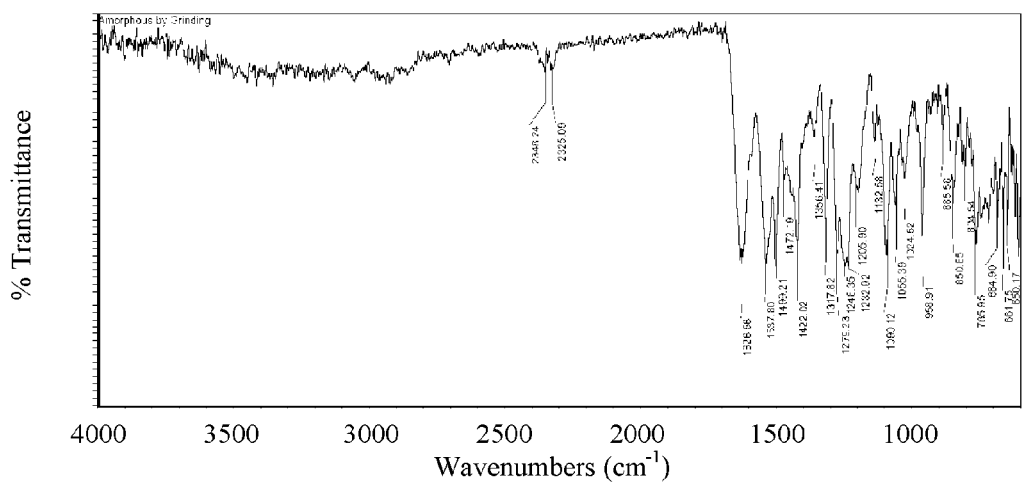
FIG. 4 illustrates a characteristic Fourier Transform Infrared (FTIR) spectrum of an amorphous form of dolutegravir sodium obtained by method I.
Figure 5:
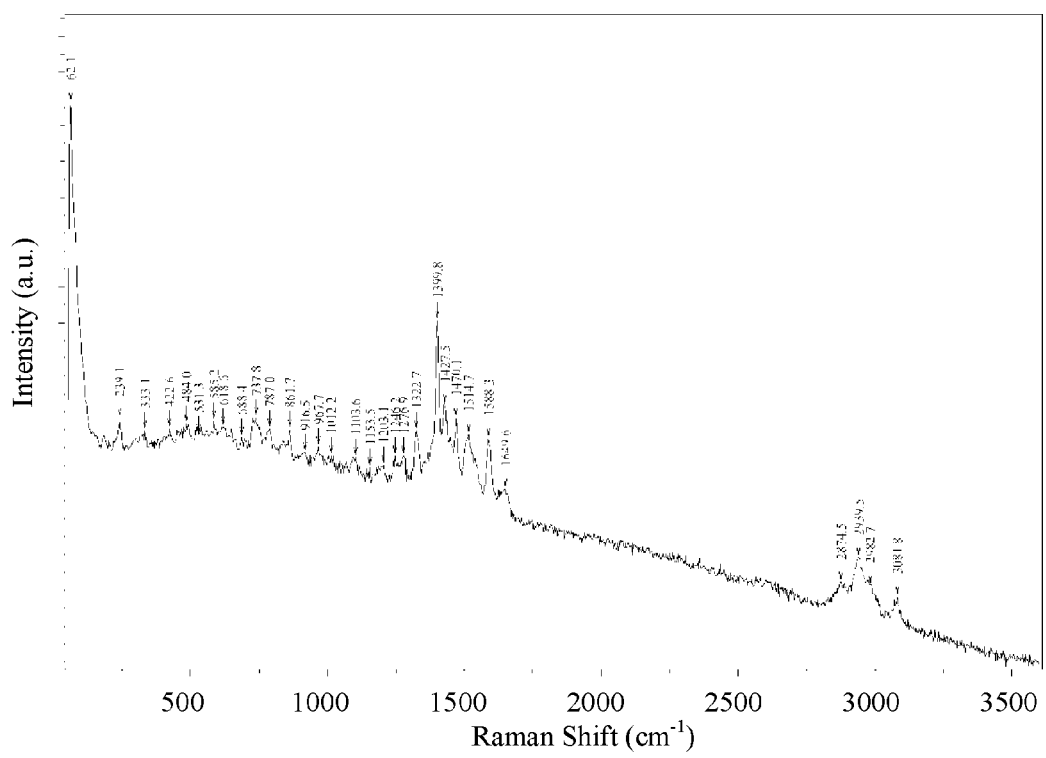
FIG. 5 illustrates a characteristic Fourier Transform-Raman (FT-Raman) spectrum of an amorphous form of dolutegravir sodium obtained by method I.

General method I was performed. Thus, dolutegravir sodium (Batch No. GVK Bio-B471-089A2) was milled by using planetary mono mill at 200 rpm for 200 or 400 min to afford amorphous dolutegravir sodium. The amorphous dolutegravir sodium obtained by this method was characterized by a broad X-ray diffraction peak between about 10 and about 30 [2θ°] characteristic of an amorphous powder (FIG. 1). FIG. 2 illustrates a characteristic DSC profile. The DSC profile shows a glass transition temperature of 208.26° C. with an onset of 201.37° C. FIG. 3 illustrates a characteristic TGA profile with a weight loss of about 2.73% between about 30° C. and about 310° C. and a weight loss of about 35.87% between about 310° C. and about 449° C. FIG. 4 illustrates a characteristic IR spectrum with peaks at about 650, 662, 685, 766, 805, 851, 886, 959, 1025, 1055, 1090, 1133, 1206, 1233, 1248, 1279, 1318, 1356, 1422, 1472, 1499, 1538, 1627, 2325 and 2348 cm$^{-1}$. FIG. 5 illustrates a characteristic FT-Raman spectrum with peaks at about 62, 239, 333, 423, 484, 531, 585, 619, 688, 738, 787, 862, 917, 968, 1012, 1104, 1154, 1203, 1246, 1277, 1323, 1400, 1428, 1470, 1515, 1588, 1650, 2875, 2940, 2983 and 3082 cm$^{-1}$.

Example 3

Amorphous Dolutegravir Sodium (Method II)

Figure 9:
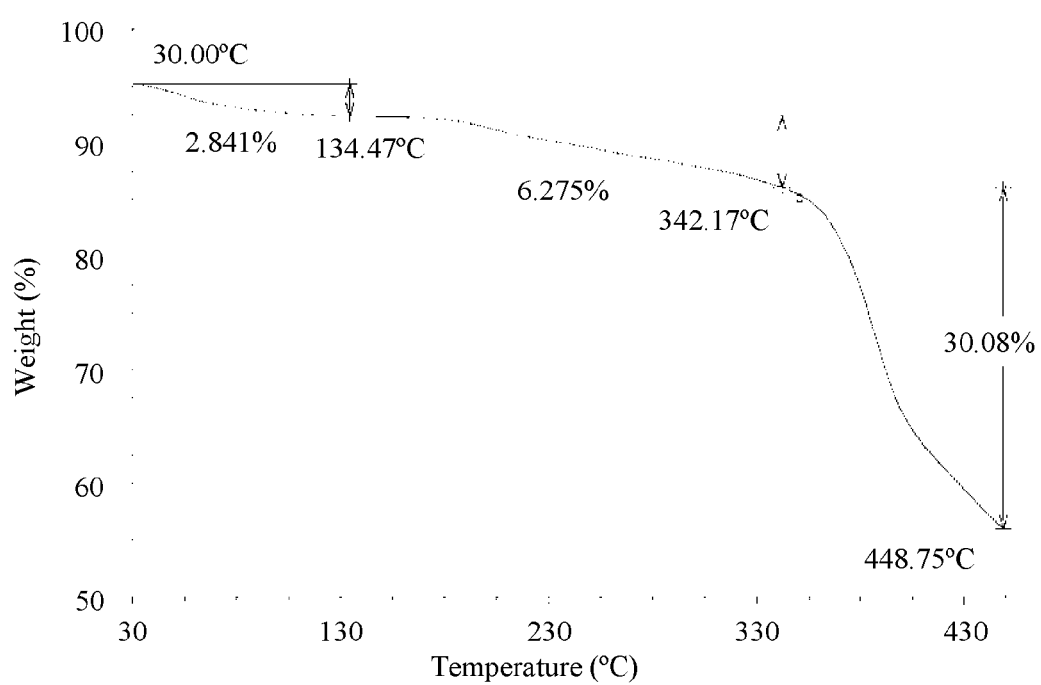
FIG. 9 illustrates a characteristic Thermogravimetric analysis (TGA) profile of an amorphous form of dolutegravir sodium obtained by method II.
Figure 10:
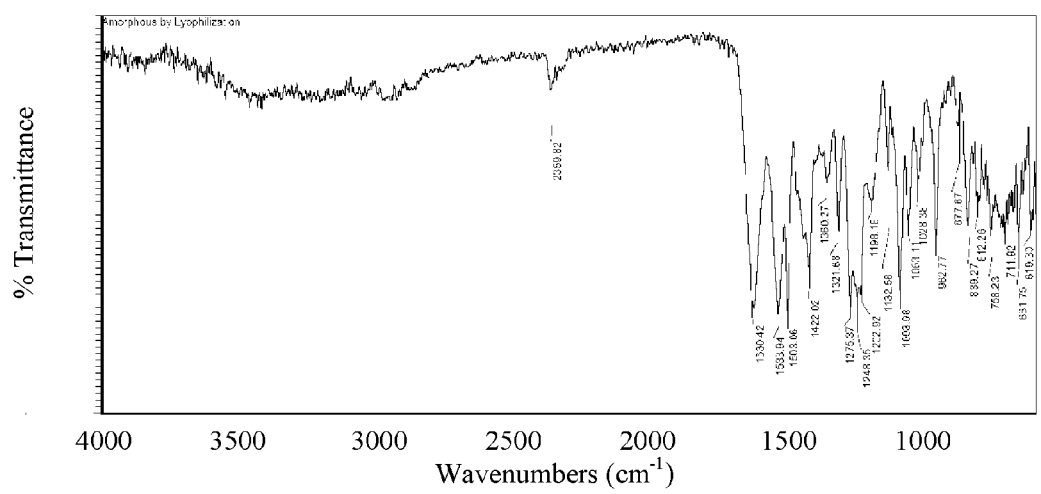
FIG. 10 illustrates a characteristic Fourier Transform Infrared (FTIR) spectrum of an amorphous form of dolutegravir sodium obtained by method II.
Figure 11:
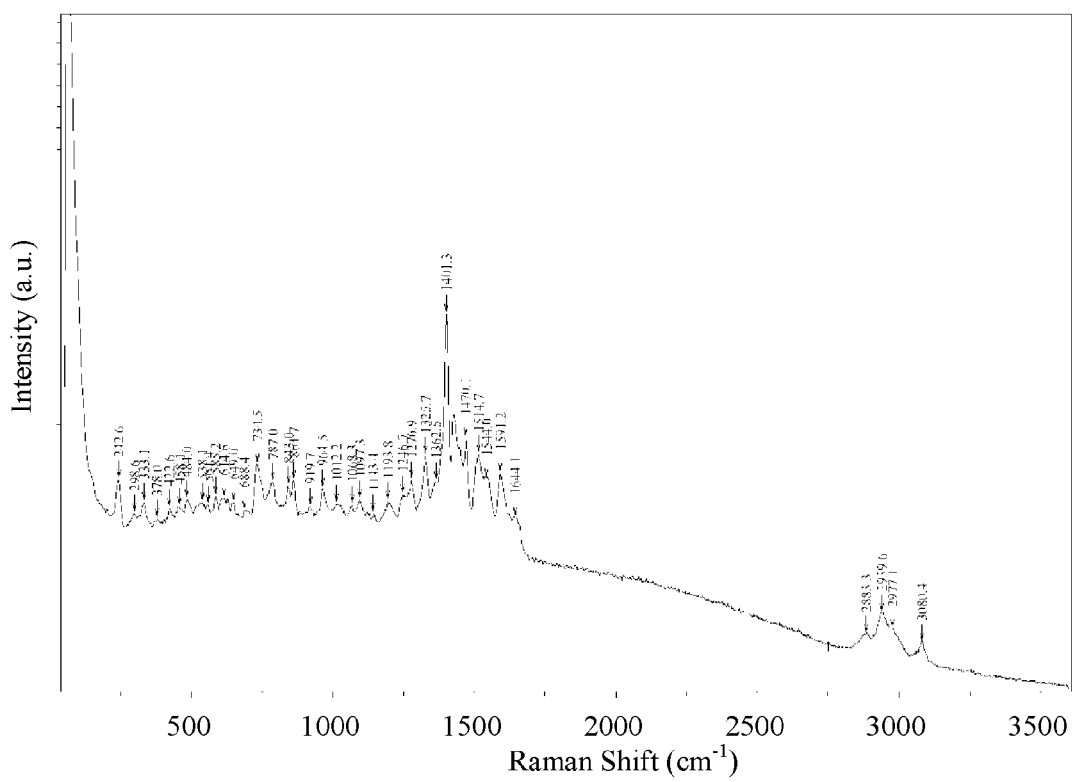
FIG. 11 illustrates a characteristic Fourier Transform-Raman (FT-Raman) spectrum of an amorphous form of dolutegravir sodium obtained by method II.

General method II was performed. Thus, dolutegravir sodium (Batch No. GVK Bio-B471-089A2; about 100 mg) was dissolved in 300 ml of water. The water was then removed by freeze-drying (lyophilization) to afford amorphous dolutegravir sodium. FIG. 6 (panel A) and FIG. 7 show characteristic XRPD of the amorphous form obtained by this method. FIG. 8 illustrates a characteristic DSC profile. The glass transition temperature of the amorphous form obtained by this method is 132.64° C. with an onset of 96.12° C. FIG. 9 illustrates a characteristic TGA profile with a weight loss of about 2.84% between about 30° C. and about 135° C., a weight loss of about 6.28% between about 135° C. and about 342° C., and a weight loss of about 30.08% between about 342° C. and about 449° C. FIG. 10 illustrates a characteristic IR spectrum with peaks at about 619, 662, 712, 758, 812, 839, 878, 963, 1028, 1063, 1094, 1133, 1198, 1233, 1248, 1275, 1322, 1360, 1422, 1503, 1534, 1630 and 2360 cm$^{-1}$. FIG. 11 illustrates a characteristic FT-Raman spectrum with peaks at about 243, 299, 333, 378, 423, 458, 484, 538, 561, 585, 615, 649, 688, 735, 787, 843, 862, 920, 965, 1012, 1068, 1097, 1143, 1194, 1247, 1277, 1326, 1363, 1401, 1470, 1515, 1544, 1591, 1644, 2883, 2940, 2977 and 3080 cm$^{-1}$. The IR and Raman spectra of the amorphous dolutegravir sodium obtained by this method are substantially similar to the spectra of the amorphous dolutegravir sodium obtained by using Method I (Example 2) and could be used as alternatives for the identification of the amorphous form of the present invention.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. An amorphous form of dolutegravir sodium, characterized by at least one of: an X-ray diffraction (XRD) profile substantially as shown in any of FIGS. 1, 6A or 7, a DSC profile substantially as shown in any of FIG. 2 or 8, a TGA profile substantially as shown in any of FIG. 3 or 9, an IR spectrum substantially as shown in any of FIG. 4 or 10, or a Raman spectrum substantially as shown in any of FIG. 5 or 11.

2. The amorphous dolutegravir sodium according to claim 1, having a glass transition temperature between about 130° C. and about 210° C.

3. The amorphous dolutegravir sodium according to claim 2, having a glass transition temperature at about 133° C. or about 208° C.

4. The amorphous dolutegravir sodium according to claim 1, wherein the IR spectrum comprises characteristic peaks at about 662±4, 766±4, 851±4, 886±4, 959±4, 1025±4, 1055±4, 1090±4, 1133±4, 1206±4, 1233±4, 1248±4, 1279±4, 1318±4, 1356±4, 2325±4 and 2348±4 cm$^{-1}$.

5. The amorphous dolutegravir sodium according to claim 4, wherein the IR spectrum further comprises characteristic peaks at about 650±4, 685±4, 805±4, 1422±4, 1472±4, 1499±4, 1538±4 and 1627±4 cm$^{-1}$.

6. The amorphous dolutegravir sodium according to claim 1, wherein the Raman spectrum comprises characteristic peaks at about 62±4, 239±4, 333±4, 423±4, 484±4, 531±4, 585±4, 619±4, 688±4, 738±4, 787±4, 862±4, 917±4, 968±4, 1012±4, 1104±4, 1154±4, 1203±4, 1246±4, 1277±4, 1323±4, 1400±4, 1428±4, 1470±4, 1515±4, 1588±4, 1650±4, 2875±4, 2940±4, 2983±4 and 3082±4 cm$^{-1}$.

7. A pharmaceutical composition comprising as an active ingredient the amorphous dolutegravir sodium according to claim 1, and a pharmaceutically acceptable carrier.

8. The pharmaceutical composition according to claim 7 in the form of a tablet.

9. A method of treating a retroviral infection comprising administering to a subject in need thereof an effective amount of a composition comprising the amorphous dolutegravir sodium according to claim 1.

10. The method according to claim 9, wherein the retroviral infection is human immunodeficiency virus (HIV) infection.

11. A process for preparing amorphous dolutegravir sodium according to claim 1, the process comprising the step of grinding or milling a dolutegravir sodium so as to provide amorphous dolutegravir sodium.

12. The process according to claim 11 comprising the step of grinding or milling a crystalline dolutegravir sodium so as to provide amorphous dolutegravir sodium.

13. The process according to claim 11, wherein the grinding or milling is performed for about 200 to about 400 minutes.

14. A process for preparing amorphous dolutegravir sodium according to claim 1, the process comprising the steps of:
  (a) dissolving dolutegravir sodium in water; and
  (b) freeze-drying or lyophilizing the solution obtained in step (a), so as to provide amorphous dolutegravir sodium.

* * * * *